US007641685B2

(12) United States Patent
Richter

(10) Patent No.: US 7,641,685 B2
(45) Date of Patent: Jan. 5, 2010

(54) SYSTEM AND METHOD FOR DELIVERING A BIFURCATED STENT

(75) Inventor: Jacob Richter, Ramat Hasharon (IL)

(73) Assignee: Medinol Ltd., Tel Aviv (IL)

( * ) Notice: Subject to any disclaimer, the term of this patent is extended or adjusted under 35 U.S.C. 154(b) by 434 days.

(21) Appl. No.: 11/478,716

(22) Filed: Jun. 30, 2006

(65) Prior Publication Data

US 2006/0247756 A1 Nov. 2, 2006

Related U.S. Application Data

(60) Continuation-in-part of application No. 11/339,317, filed on Jan. 24, 2006, now Pat. No. 7,371,255, which is a continuation of application No. 10/066,755, filed on Feb. 6, 2002, now Pat. No. 6,989,026, which is a division of application No. 09/575,957, filed on May 23, 2000, now Pat. No. 6,440,165, which is a continuation-in-part of application No. 09/072,846, filed on May 5, 1998, now Pat. No. 6,251,133, which is a continuation-in-part of application No. 09/049,842, filed on Mar. 27, 1998, now Pat. No. 6,090,133, which is a continuation of application No. 08/840,612, filed on Apr. 29, 1997, now Pat. No. 5,755,734, which is a division of application No. 08/642,297, filed on May 3, 1996, now abandoned.

(51) Int. Cl.
*A61F 2/06* (2006.01)
(52) U.S. Cl. .................................................. 623/1.35
(58) Field of Classification Search ........ 623/1.11–1.36
See application file for complete search history.

(56) References Cited

U.S. PATENT DOCUMENTS 4,577,631 A 3/1986 Kreamer (Continued)

FOREIGN PATENT DOCUMENTS

AU 37832/95 5/1996

(Continued)

OTHER PUBLICATIONS

International Search Report dated Feb. 23, 2009 from co-pending application no. PCT/IB07/01792.

(Continued)

*Primary Examiner*—Suzette J Gherbi
(74) *Attorney, Agent, or Firm*—Cadwalader Wickersham & Taft LLP

(57) ABSTRACT

A system and method for delivering and assembling a bifurcated stent in a bifurcated vessel having a first lumen and a second lumen. The system and method includes the use of three balloon catheters wherein at least one of the catheters is a fixed wire catheter. A first segment of the bifurcated stent having a stem portion, a first leg portion, a longitudinal bore extending therethrough and a branch aperture formed in the side wall is mounted on two of the balloon catheters and delivered to the treatment site where it is implanted into the first lumen. A second segment of the bifurcated stent having a proximal end, a distal end and a longitudinal bore extending therethrough is mounted on the third balloon catheter and is delivered to the treatment site such that the distal end extends into the second lumen and the proximal end extends into longitudinal bore of the first segment. The second segment is then implanted into the second lumen and secured to the branch aperture of the first segment to form a bifurcated stent.

12 Claims, 16 Drawing Sheets

U.S. PATENT DOCUMENTS

| | | | |
|---|---|---|---|
| 4,733,665 A | 3/1988 | Palmaz | |
| 4,795,465 A | 1/1989 | Marten | |
| 4,896,670 A | 1/1990 | Crittenden | |
| 4,994,071 A | 2/1991 | MacGregor | |
| 5,219,355 A | 6/1993 | Parodi | |
| 5,316,023 A | 5/1994 | Palmaz | |
| 5,342,387 A | 8/1994 | Summers | |
| 5,383,892 A | 1/1995 | Cardon | |
| 5,464,449 A | 11/1995 | Ryan | |
| 5,575,817 A | 11/1996 | Martin | |
| 5,607,444 A | 3/1997 | Lam | |
| 5,609,605 A | 3/1997 | Marshall | |
| 5,609,627 A | 3/1997 | Goicoechea | |
| 5,613,980 A | 3/1997 | Chauhan | |
| 5,617,878 A | 4/1997 | Taheri | |
| 5,628,783 A * | 5/1997 | Quiachon et al. | 623/1.35 |
| 5,632,763 A | 5/1997 | Glastra | |
| 5,669,924 A | 9/1997 | Shaknovich | |
| 5,676,697 A | 10/1997 | McDonald | |
| 5,679,659 A | 10/1997 | Verhoeven | |
| 5,707,386 A | 1/1998 | Schnepp-Pesch | |
| 5,723,004 A | 3/1998 | Dereume | |
| 5,725,572 A | 3/1998 | Lam | |
| 5,749,375 A | 5/1998 | Maginot | |
| 5,755,734 A | 5/1998 | Richter | |
| 5,755,735 A | 5/1998 | Richter | |
| 5,755,771 A | 5/1998 | Penn et al. | |
| 5,766,238 A | 6/1998 | Lau et al. | |
| 5,782,906 A | 7/1998 | Marshall | |
| 5,824,042 A | 10/1998 | Lombardi | |
| 5,824,043 A | 10/1998 | Cottone | |
| 5,824,052 A | 10/1998 | Khosravi | |
| 5,824,056 A | 10/1998 | Rosenberg | |
| 5,827,320 A | 10/1998 | Richter | |
| 5,833,707 A | 11/1998 | McIntyre | |
| 5,843,160 A | 12/1998 | Rhodes | |
| 5,855,598 A | 1/1999 | Pinchuk | |
| 5,861,027 A | 1/1999 | Trapp | |
| 5,906,640 A | 5/1999 | Penn | |
| 5,906,641 A | 5/1999 | Thompson | |
| 5,916,263 A | 6/1999 | Goicoechea | |
| 5,944,019 A | 8/1999 | Knudson | |
| 5,961,548 A | 10/1999 | Shmulewitz | |
| 5,972,017 A | 10/1999 | Berg | |
| 5,984,955 A | 11/1999 | Wisselink | |
| 6,017,363 A | 1/2000 | Hojeibane | |
| 6,033,434 A | 3/2000 | Borghi | |
| 6,033,435 A | 3/2000 | Penn | |
| 6,056,775 A | 5/2000 | Borghi | |
| 6,090,133 A | 7/2000 | Richter | |
| 6,096,073 A | 8/2000 | Webster | |
| 6,102,938 A | 8/2000 | Evans | |
| 6,110,198 A | 8/2000 | Fogarty | |
| 6,117,117 A | 9/2000 | Mauch | |
| 6,117,156 A | 9/2000 | Richter | |
| 6,129,738 A | 10/2000 | Lashinski | |
| 6,136,022 A | 10/2000 | Nunez et al. | |
| 6,142,973 A | 11/2000 | Carleton | |
| 6,149,682 A | 11/2000 | Frid | |
| 6,162,243 A | 12/2000 | Gray | |
| 6,165,195 A | 12/2000 | Wilson | |
| 6,183,509 B1 | 2/2001 | Dibie | |
| 6,190,353 B1 | 2/2001 | Makower | |
| 6,193,745 B1 | 2/2001 | Fogarty | |
| 6,203,568 B1 | 3/2001 | Lombardi | |
| 6,210,429 B1 | 4/2001 | Vardi | |
| 6,224,609 B1 * | 5/2001 | Ressemann et al. | 606/108 |
| 6,251,133 B1 | 6/2001 | Richter | |
| 6,258,116 B1 | 7/2001 | Hojeibane | |
| 6,290,673 B1 | 9/2001 | Shanley | |
| 6,325,826 B1 | 12/2001 | Vardi | |
| 6,346,089 B1 | 2/2002 | Dibie | |
| 6,406,489 B1 | 6/2002 | Richter | |
| 6,436,104 B2 | 8/2002 | Hojeibane | |
| 6,436,134 B2 | 8/2002 | Richter | |
| 6,440,165 B1 | 8/2002 | Richter | |
| 6,520,987 B1 | 2/2003 | Plante | |
| 6,520,988 B1 * | 2/2003 | Colombo et al. | 623/1.35 |
| 6,540,779 B2 | 4/2003 | Richter | |
| 6,599,316 B2 | 7/2003 | Vardi | |
| 7,172,619 B2 * | 2/2007 | Richter | 623/1.11 |

FOREIGN PATENT DOCUMENTS

| | | |
|---|---|---|
| DE | 29701758 | 5/1997 |
| EP | 0551179 | 7/1993 |
| EP | 0669114 A1 | 2/1995 |
| EP | 0686379 | 2/1995 |
| EP | 0804907 | 11/1997 |
| EP | 0916317 | 5/1999 |
| EP | 0943303 | 9/1999 |
| EP | 0956832 | 11/1999 |
| FR | 2064228 | 7/1971 |
| FR | 2678508 | 1/1993 |
| GB | 1299963 | 12/1972 |
| SU | 942736 | 7/1982 |
| WO | WO 95/16406 | 6/1995 |
| WO | WO 95/21592 | 8/1995 |
| WO | WO 96/34580 | 11/1996 |
| WO | WO 96/41592 | 12/1996 |
| WO | WO 97/33532 | 9/1997 |
| WO | WO 97/46174 | 12/1997 |
| WO | WO 98/19628 | 5/1998 |
| WO | WO 98/36708 | 8/1998 |
| WO | WO 00/44307 | 8/2000 |
| WO | WO 01/74273 | 10/2001 |

OTHER PUBLICATIONS

International Preliminary Report on Patentability and Written Opinion dated Jul. 28, 2009 from co-pending application No. PCT/IB07/01792.

* cited by examiner

SYSTEM AND METHOD FOR DELIVERING A BIFURCATED STENT

CROSS-REFERENCE TO RELATED APPLICATIONS

This application is a continuation-in-part of application Ser. No. 11/339,317, filed Jan. 24, 2006, now U.S. Pat. No. 7,371,255, which is a continuation of application Ser. No. 10/066,755, filed Feb. 6, 2002, now U.S. Pat. No. 6,989,026, which is a division of application Ser. No. 09/575,957 filed May 23, 2000, now U.S. Pat. No. 6,440,165, which is a continuation-in-part of application Ser. No. 09/072,846, filed May 5, 1998, now U.S. Pat. No. 6,251,133, which is a continuation-in-part of application Ser. No. 09/049,842, filed Mar. 27, 1998, now U.S. Pat. No. 6,090,133, which is continuation of application Ser. No. 08/840,612, filed on Apr. 29, 1997, now U.S. Pat. No. 5,755,734, which is a division of application Ser. No. 08/642,297, filed May 3, 1996, now abandoned.

FIELD OF THE INVENTION

The present invention relates to stents, and more particularly methods of delivering a bifurcated stent.

BACKGROUND OF THE INVENTION

Stents are well known in the art. They are typically formed of a cylindrical metal mesh, which can expand when pressure is internally applied. Alternatively, they can be formed of wire wrapped into a cylindrical shape or sheets of material formed into a cylindrical shape.

Stents are devices that are usually implanted within bodily conduits including the vascular system to reinforce collapsing, partially occluded, weakened, or abnormally dilated sections of the blood vessel. Stents also have been successfully implanted in other areas, e.g., the urinary tract or the bile duct to reinforce such bodily conduits.

U.S. Pat. No. 4,994,071 (MacGregor) discloses an expandable, bifurcating stent having a main cylindrical lattice formed from interconnected, flexible wire. Two additional cylindrical lattices, having smaller diameters than the main lattice, are similarly constructed. The main lattice includes a flexible wire interconnecting the main lattice to one of the additional lattices. A second flexible wire interconnects the main lattice to the other additional lattice. The flexible wires form backbones that extend axially along the length of the main lattice and along each of the additional lattices. One disadvantage of this bifurcating stent is the complex nature of the interconnection of the flexible wires forming the backbones with the loop structure of each lattice.

Thus, embodiments described in the aforementioned U.S. Pat. No. 6,251,133 provide methods of making a stent which includes a first tubular member having a branch aperture. The tubular member may be inserted in a blood vessel, for example, with the branch aperture aligned with a side branch vessel. A second tubular member having a longitudinal bore may then be disposed and secured within the branch aperture of the first tubular member and, for example, extending into the branch vessel, with the longitudinal bore of the second tubular member in fluid communication with the longitudinal bore of the first tubular member.

Typically, two "over-the-wire" balloon catheters are used for delivering and implanting a bifurcated stent. One of the catheters delivers a portion of the bifurcated stent to the main vessel and the other catheter delivers a portion of the bifurcated to the side branch lumen. Each catheter has a lumen which is dimensioned to receive a guide wire. The guide wires are routed through the vasculature such that the distal end of one of the guide wires extends beyond the target site in the main vessel and the distal end of the other guide wire extends beyond the target site in the side branch lumen. The proximal end of each guide wire is then inserted into the distal end of the guide wire lumen of one of the catheters and the catheters are routed through the vasculature over the guide wires to the target site. When the bifurcated stent portions are positioned within the treatment site, the catheter balloons are inflated and the stent portions are expanded and implanted into the vessel walls. The stent portions may be delivered to and/or implanted at the target site together or sequentially.

The use of two "over-the-wire" catheters with separate guide wires can result in wire crossings within the vasculature which may create confusion to the physician as to which of the guide wires leads to the main vessel and which of the guide wires leads to the side branch lumen. This can result in a significant delay in the procedure. For example, if the catheter carrying the stent portion intended for the main vessel is advanced along the guide wire leading to the side branch lumen, the distal ends of the guide wires must be switched between the main vessel and the side branch lumen or the catheter must be withdrawn from the guide wire and reinserted onto the other guide wire. However, the most serious problem resulting from such wire crossings occurs during the advancement of the two "over-the-wire" catheters on the wires. Specifically, when the two catheters reach the point of a wire crossing, the catheters are positively stopped at that position and cannot be advanced any further along the guide wires. Under these circumstances, the only solution is to withdraw at least one of the guide wires and reposition it within the vasculature. This is both risky and time consuming. Further, when the catheters are advanced toward the treatment site together, the combined profiles of the portions of the catheters with the guide wire lumens may prevent insertion through constricted areas of the vasculature.

One particular delivery method of a bifurcated stent, such as the stents disclosed in U.S. Pat. No. 6,251,133, to the target area includes mounting the stent on two expandable balloons of the same length. Both expandable balloons are advanced along separate guide wires toward the target site together, or are advanced individually in sequential order. One expandable balloon is to be disposed in the main vessel, and one the other is to be disposed in the side branch lumen of the bifurcated vessel. Typically, the side branch balloon is the same length or shorter than the main vessel balloon. Upon reaching the target area in the vessel, the main vessel becomes very crowded due to both balloons filling up the lumen of the main vessel. This causes the tip of the side branch balloon to be pressed against the main vessel, and causes difficulty in orienting the balloon into the side branch lumen, and hinders the ability of the side branch balloon to bend into the side branch vessel.

SUMMARY OF THE INVENTION

Embodiments of the present invention solves these and other disadvantages of the prior art by providing a side branch balloon catheter whose tip leads the tip of the main vessel balloon catheter by few millimeters, so that the side branch balloon leads the delivery system while advancing towards the target area. The side branch balloon catheter reaches the target area first, allowing for greater freedom of the side branch balloon to bend into the aperture of the side branch vessel, due to less crowding of balloon catheter in the main vessel.

Another embodiment of the present invention provides a bifurcated stent delivery system having one over the wire catheter and one fixed wire catheter. This system only requires one guide wire and, therefore, eliminates any possible confusion that may result from wire crossing in the vasculature. The use of a single guide wire in this system also eliminates the possibility of wire crossings that result in the catheters becoming positively stopped at and unable to be advanced beyond the location of the wire crossing. In addition, since the fixed wire catheter does not include a guide wire lumen and thus has a smaller profile than an over-the-wire catheter, this system provides a smaller combined profile which enables the system to pass through more severe constrictions in the vasculature when the catheters are advanced to the target site together.

DETAILED DESCRIPTION

Figure 1:
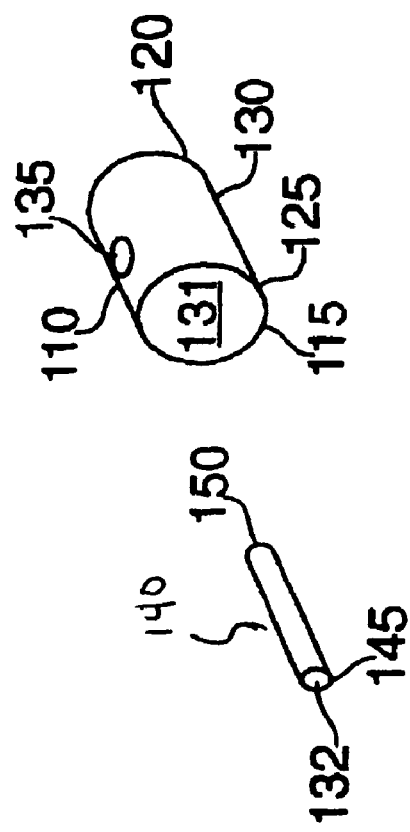
FIG. 1 shows a stem and first leg portion and a second leg portion used to form an embodiment of a bifurcated stent manufactured in accordance with this invention.

FIG. 1 is a general representation of one type of a stent with which the present invention may be used. The stent comprises two portions, which are deployed serially in two steps and assembled within the patient to form a bifurcated stent. FIG. 1 shows stem and first leg portion 110 provided with a longitudinal bore 131 and having a proximal end 115 defining a stem portion 125 and a distal end 120. Second leg portion 140 is provided with a longitudinal bore 132 and has a proximal end 145 and a distal end 150. Stem and first leg portion 110 and second leg portion 140 may be sized and patterned or etched as previously discussed. A branch aperture 135 is disposed between the proximal end 115 and the distal end 120 of stem and first leg portion 110. The branch aperture 135 is sized to receive second leg portion 140 and is adapted to engage and secure the second leg portion 140 when it has been expanded within the branch aperture 135. Second leg portion 140 is sized and adapted to engage and be secured into branch aperture 135 upon expansion.

Figure 2:
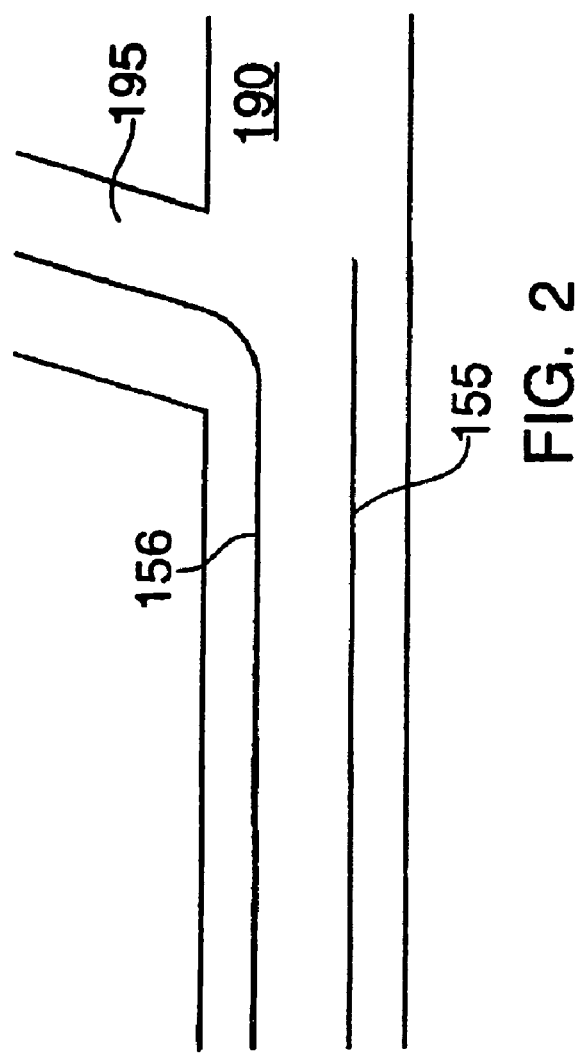
FIG. 2 shows guide wires disposed in the trunk lumen and branch lumen to be treated.

FIGS. 2 to 9 show how the bifurcated stent is assembled within a bifurcated lumen. As shown in FIGS. 2 to 9, the area to be treated is a bifurcated lumen having a first or trunk lumen 190 and a second or branch lumen 195. As shown in FIG. 2, a first guide wire 155 is introduced into the main lumen 190 and a second guide wire 156 is introduced into the branch lumen 195.

Figure 3:
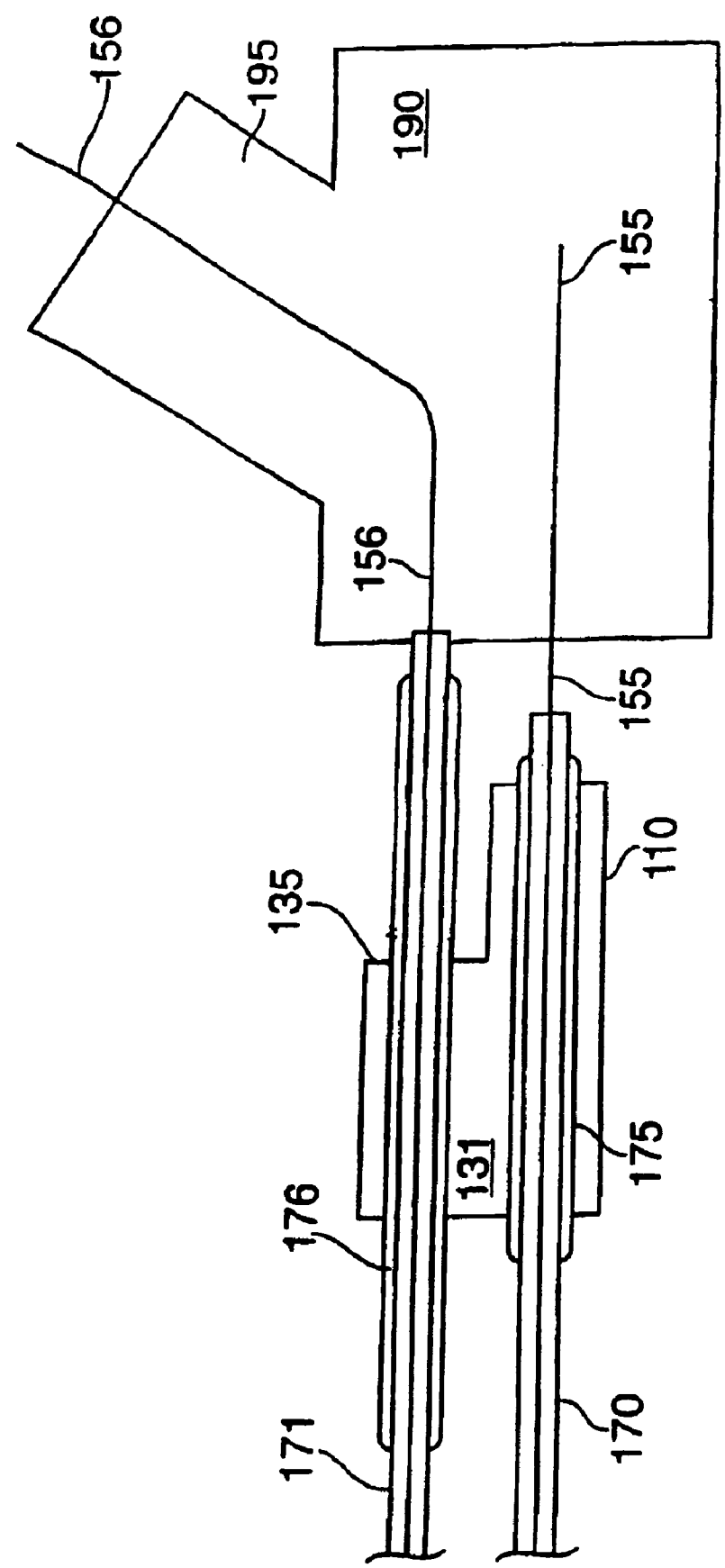
FIG. 3 shows the stem and first leg portion shown in FIG. 1 disposed on catheters and guide wires prior to introduction into the lumen to be treated.

As shown in FIG. 3, a balloon expandable stem and first leg portion 110 of a bifurcated stent is disposed on the tip of a first balloon catheter 170 so that the balloon 175 is disposed within a longitudinal bore 131. A second balloon catheter 171 is then introduced into longitudinal bore 131 of stem and first leg portion 110 and is advanced so that the balloon 176 is disposed within aperture 135, with its tip extending further forward than the tip of the first balloon catheter 170. As illustrated, the tip of balloon 176 leads the whole system. First catheter 170 is then mounted on first guide wire 155 and second catheter 171 is mounted on second guide wire 156. The balloon lengths are selected in conventional fashion; the balloon 176 may be shorter or longer than the balloon 175, so long as its tip is positioned so as to lead.

Figure 4:
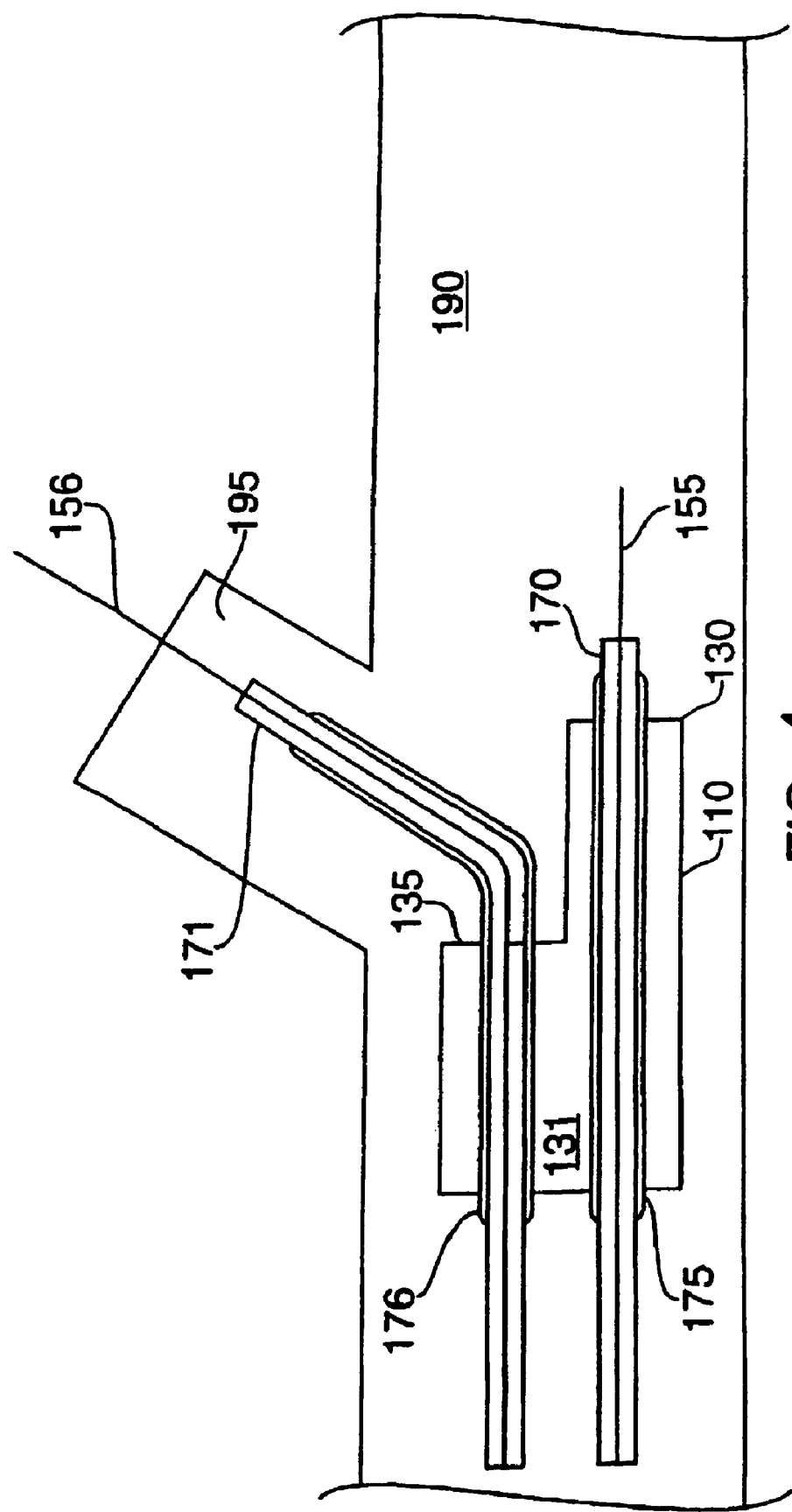
FIG. 4 shows the stem and first leg portion shown in FIG. 1 after it has been delivered to the bifurcation to be treated and prior to its expansion.

As shown in FIG. 4, the unexpanded stem and first leg portion 110 is guided to the area to be treated so that first leg portion 130 is disposed within trunk lumen 190 and branch aperture 135 communicates with branch lumen 195. Because the tip of balloon catheter leads the whole system, it is able to get into the side branch 195 before the rest of the system reaches the area. This greatly facilitates entry of the catheter into, and alignment of the branch aperture 135 with, the side branch 195.

Figure 5:
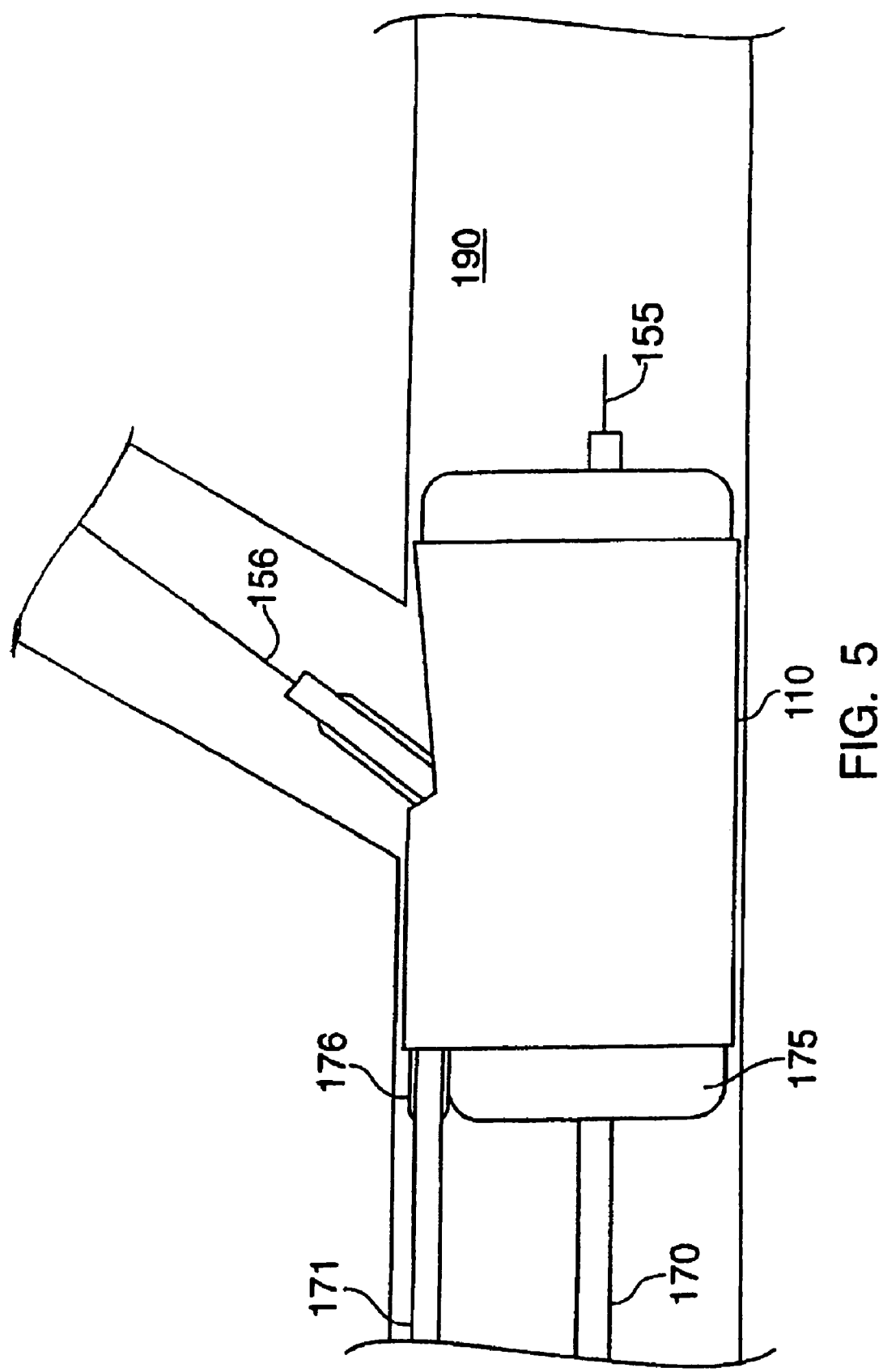
FIG. 5 shows the stem and first leg portion shown in FIG. 4 after it has been expanded.
Figure 6:
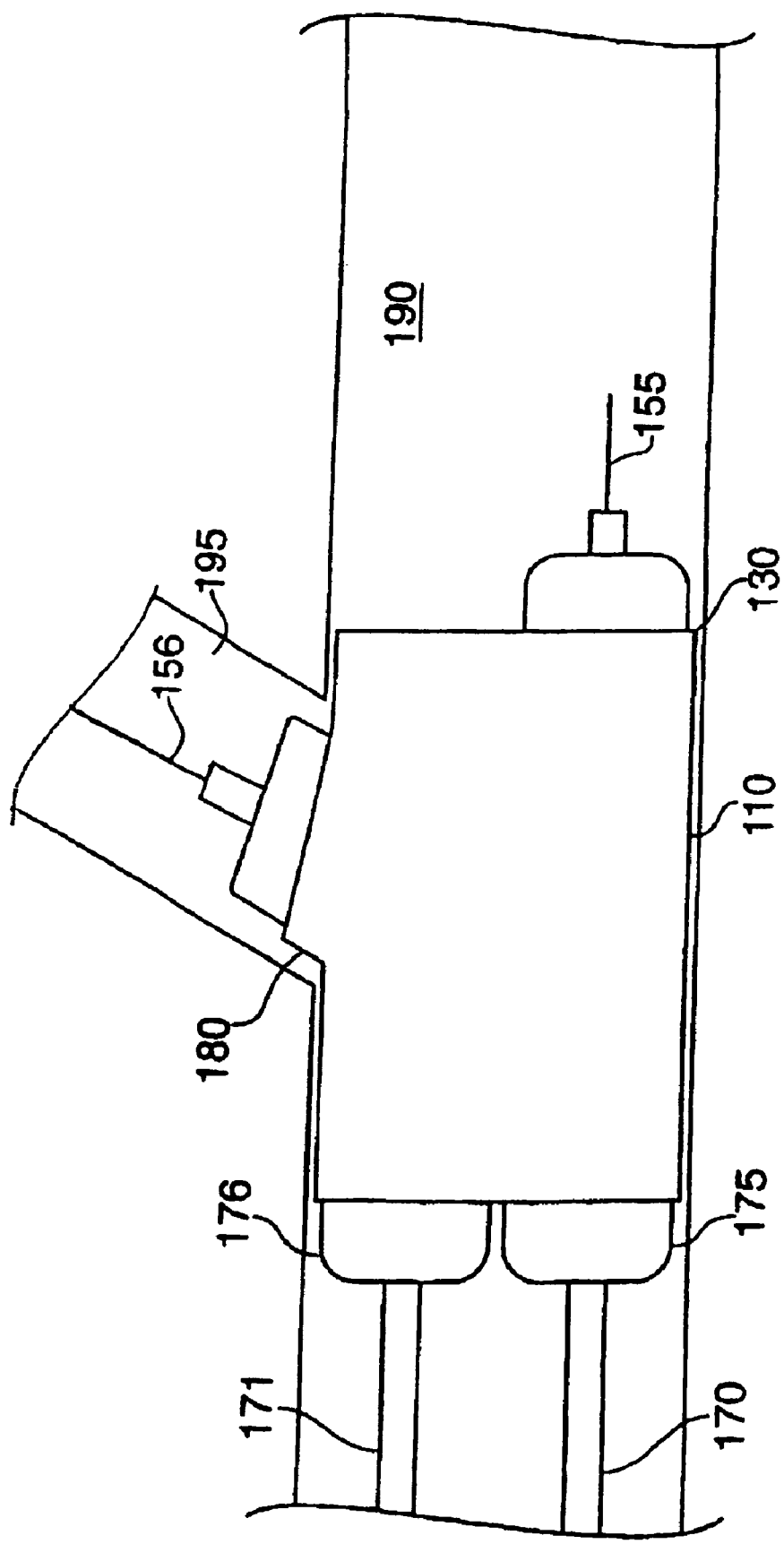
FIG. 6 shows expansion of the branch aperture.

Guide wire 156 facilitates the orientation of the branch aperture 135 with the branch lumen 195. The size of the conventional catheters and balloons is not to scale and details well known to those skilled in the art have been omitted for clarity. In one embodiment, balloon 175 is inflated which causes the stem and first leg portion 110 to expand, as shown in FIG. 5, to secure it in the desired position. After expansion, the external wall of stem and first leg portion 110 would contact the interior walls of trunk lumen 190; however, a gap has been intentionally left for clarity. The balloon 175 on first catheter 170 is left inflated and the balloon 176 on second catheter 171 is then inflated to enlarge the branch aperture 135 as shown in FIG. 6. As the branch aperture 135 is enlarged a portion of the stent defining the branch aperture 135 is pushed outward to form a branch securing lip 180.

Figure 7:
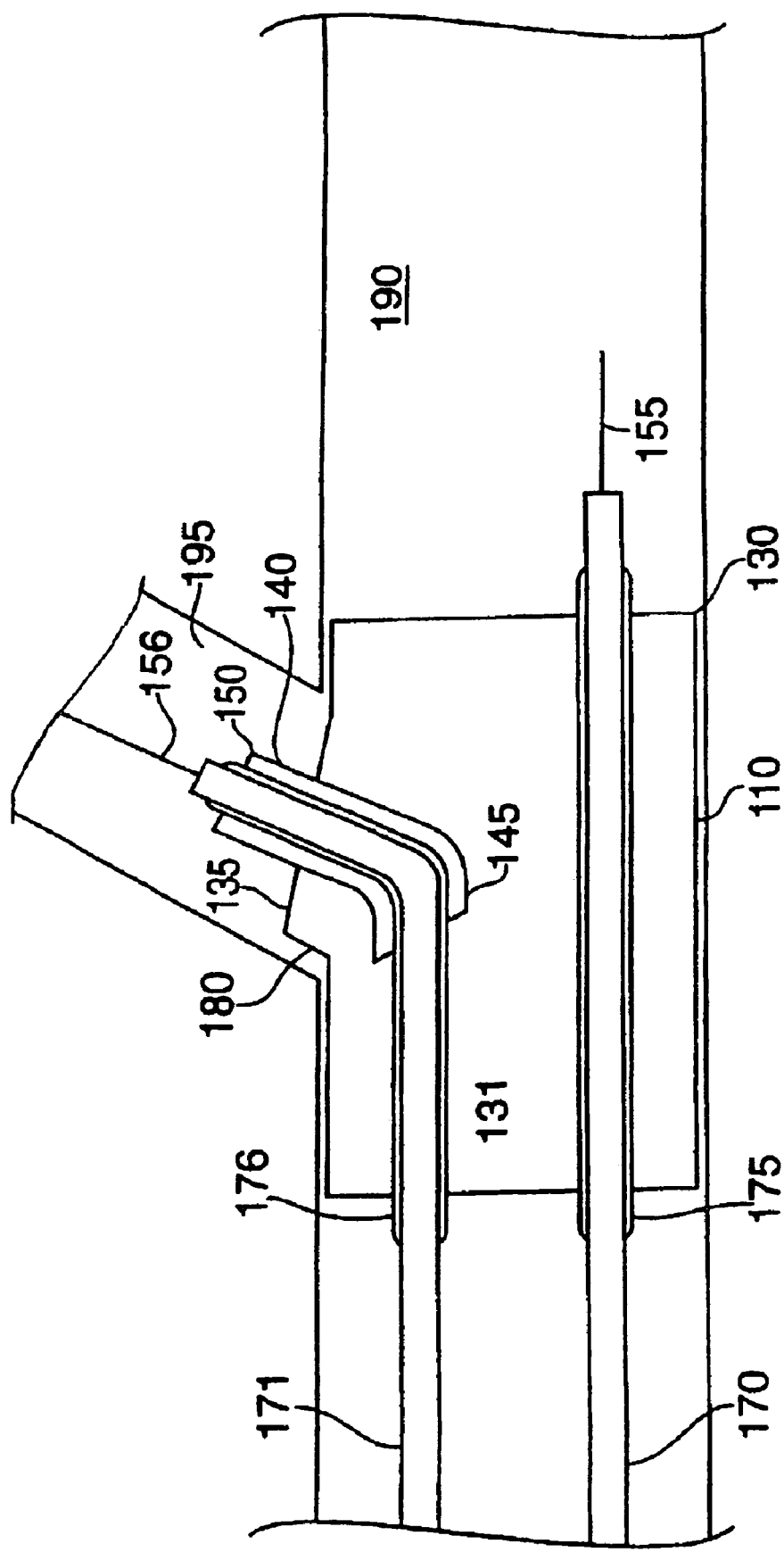
FIG. 7 shows the unexpanded second leg portion disposed in the branch aperture.

In this embodiment, balloons 175 and 176 are deflated, second catheter 171 is withdrawn, and second guide wire 156 is left in place in the branch lumen 195. Second leg portion 140 is then applied to second catheter 171 so that balloon 176 is disposed in longitudinal bore 132 and second catheter 171 is then applied to second guide wire 156. Second leg portion 140 is then guided to, and introduced into, the longitudinal bore 131 of the stem and first leg portion 110 and is advanced and passed through branch aperture 135 so that the distal end 150 of the second leg portion 140 protrudes into the branch lumen 195 and the proximal end 145 communicates with longitudinal bore 131, as shown in FIG. 7. The balloon 176 on second catheter 171 is partially inflated and the balloon 175 on first catheter 170 is then partially inflated to a pressure substantially equal to the pressure in balloon 176. Both balloons 175 and 176 are then simultaneously inflated to substantially equal pressures.

Figure 8:
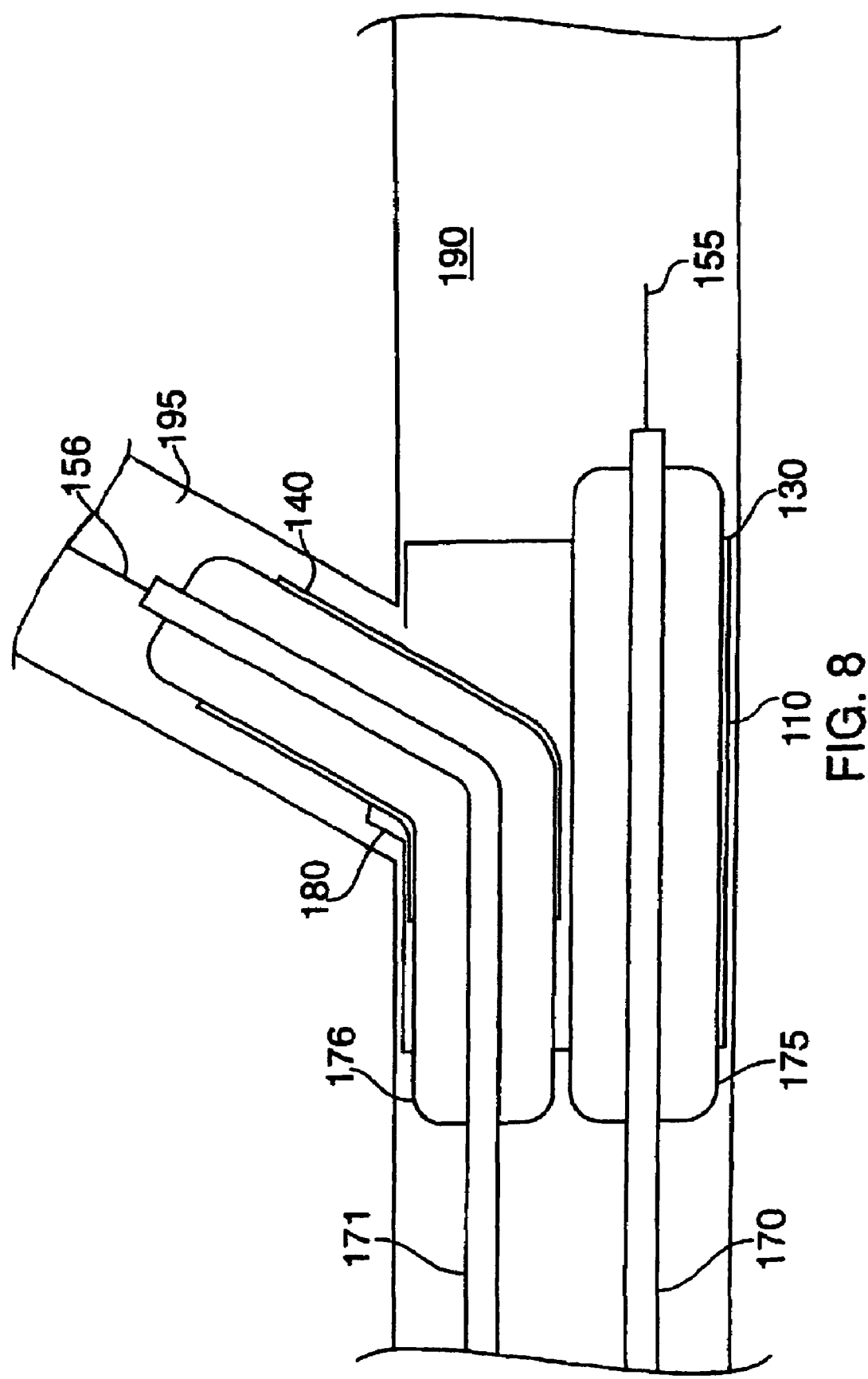
FIG. 8 shows the expansion of the second leg portion shown in FIG. 7.
Figure 9:
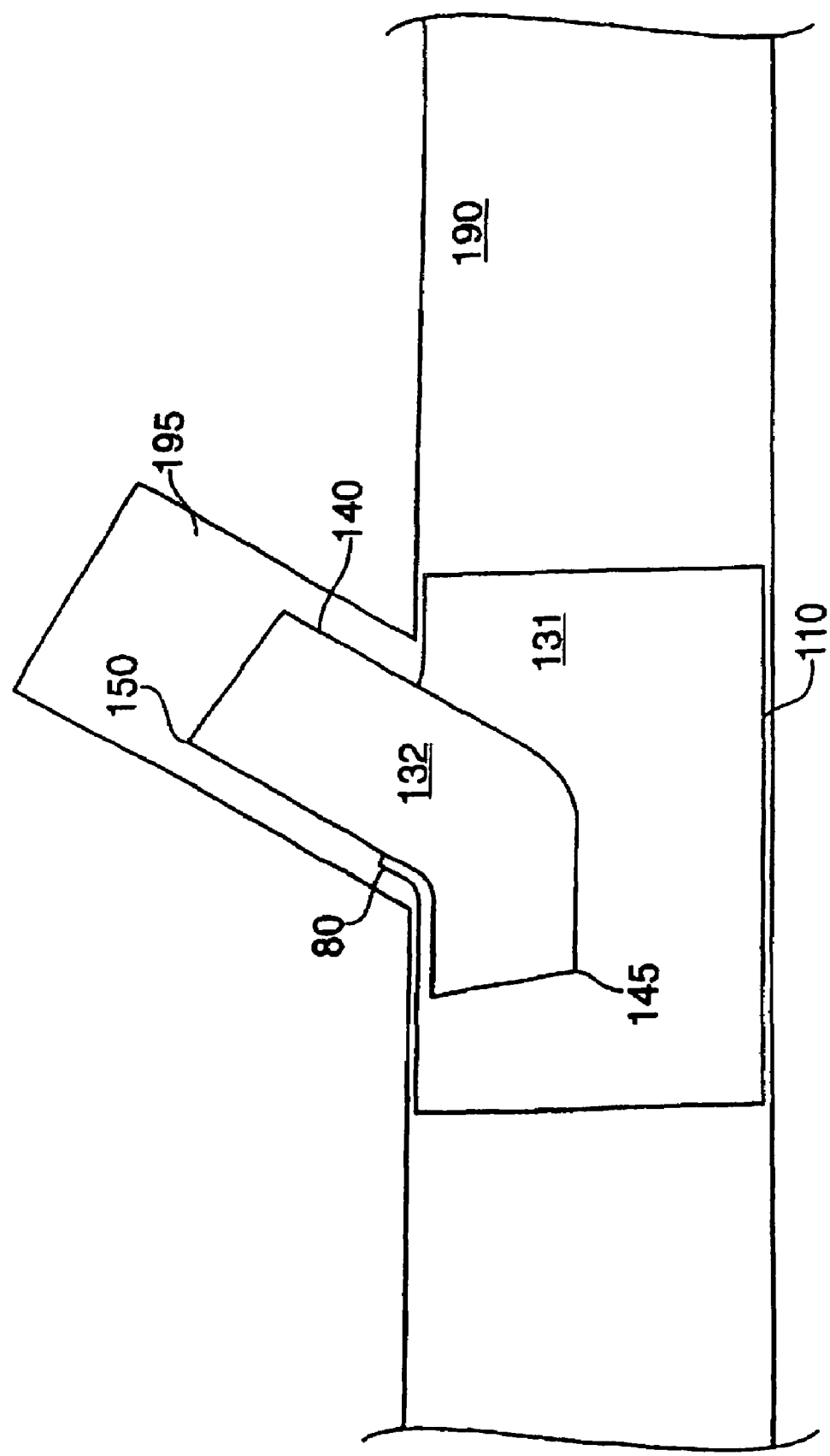
FIG. 9 shows the assembled bifurcated stent disposed in the bifurcated lumen to be treated.

As shown in FIG. 8, inflation of the balloon 176 on second catheter 171 causes second leg member 140 to expand so that its external walls engage and are secured to the area surrounding aperture 135. Inflation of the balloon 175 on the first catheter 170 prevents stem and first leg portion 110 from collapsing when balloon 176 is inflated. After expansion, the external walls of second leg 140 would contact the inner wall of lumen 195; however, a gap has been intentionally left for clarity. The balloons 175 and 176 are deflated, catheters 170 and 171 and guide wires 155 and 156 are withdrawn, and the assembled bifurcated stent 160 is left in place as shown in FIG. 9.

An alternative embodiment of a method of making a bifurcated stent comprises the steps of preparing a first expandable tubular member 110 having a proximal end 115 and a distal end 120 and a longitudinal bore 131 therethrough. The first tubular member 110 is provided with a branch aperture 135 disposed between the proximal end 115 and the distal end 120. The branch aperture 135 communicates with the longitudinal bore 131 of the first expandable tubular member 110 and the aperture 135 is sized and adapted to receive and secure a second expandable tubular member 140. The first expandable tubular member 110 is delivered to a bifurcated vessel having a first lumen 190 and a second lumen 195 so that the first expandable tubular member 110 is disposed within the first lumen 190 and the branch aperture 135 communicates with the second lumen 195. The branch aperture 135 is aligned with the second lumen 195 and may be widened by first inflating the balloon 176 of FIG. 4. As specific applications dictate, the portion of the first expandable tubular member defining the branch aperture 135 may be adapted to form a branch securing lip when the branch aperture 135 is expanded a sufficient amount by inflating the balloon 176.

As shown in FIG. 5, the first expandable tubular member 110 is then expanded an amount sufficient to secure the first expandable tubular member 110 in the first lumen 190. A second expandable tubular member 140 is prepared having a proximal end 145 and a distal end 150 having longitudinal bore 132 therethrough. The second expandable tubular member 140 is delivered into the branch aperture 135 so that the distal end 150 of the second expandable tubular member 140 is disposed within the second lumen 195 and the proximal end 145 of the second expandable tubular member 140 is disposed within the branch aperture 135 of the first tubular member 110 and so that the longitudinal bore 132 of the second expandable tubular member 140 is in fluid communication with the longitudinal bore 131 of the first longitudinal tubular member 110. As shown in FIG. 6, the second expandable tubular member 140 is then expanded in an amount sufficient to secure the second expandable tubular member 140 within the second lumen 195 and within the branch aperture 135 of the first expandable tubular member 110.

In one particular embodiment, a first guide wire 155 is delivered into the first lumen 190 of a bifurcated vessel having a first lumen 190 and a second lumen 195 and a second guide wire 156 is delivered into the second lumen 195 of the bifurcated vessel. A first expandable tubular member 110 is prepared having a proximal end 115 and a distal end 120 and a longitudinal bore 131 therethrough. The first expandable tubular member 110 is provided with a branch aperture 135 disposed between the proximal end 115 and the distal end 120. The branch aperture 135 communicates with the longitudinal bore 131 and the branch aperture 135 is sized and adapted to receive and secure a second expandable tubular member 140. The first expandable tubular member 110 is mounted on a first balloon catheter 170 and the first balloon catheter 170 is mounted on the first guide wire 155.

The first expandable tubular member 110 is delivered to the first lumen 190 of the bifurcated vessel so that the first expandable tubular member 110 is disposed within the first lumen 190 and the branch aperture communicates 135 with the second lumen 195. A second balloon catheter 171 is mounted on the second guide wire 156 and the balloon portion 176 of the second balloon catheter 171 is delivered into the side-branch aperture 135. In accordance with the present invention, both balloons may be inserted through the stem portion of the tubular member and delivered to the bifurcated vessel simultaneously. As explained previously, the tip of balloon catheter 171 leads the whole system, permitting it to be more easily aligned with and inserted in the branch lumen 195.

The second balloon catheter 171 is inflated to align the branch aperture 135 with the second lumen 195. It may additionally be inflated sufficiently to widen the branch aperture 135. The first balloon catheter 170 may then be inflated to expand the first expandable member 110 in an amount sufficient to secure the first expandable member 110 in the first lumen 190. The first 170 and second 171 balloon catheters are deflated and the second balloon catheter 171 is removed.

A second expandable tubular member 140 is prepared having a proximal end 145 and a distal end 150 having longitudinal bore 132 therethrough. The second expandable tubular member 140 is mounted on the second balloon catheter 171. The second expandable tubular member 140, mounted on the second balloon catheter 171, is delivered into the branch aperture 135 so that the distal end 150 of the second expandable tubular member 140 is disposed within the second lumen 195 and the proximal end 145 of the second expandable tubular member 140 is disposed within the branch aperture 135 of the first tubular member 110 and so that the longitudinal bore 132 of the second expandable tubular member 140 is in fluid communication with the longitudinal bore 131 of the first longitudinal member 110. The first balloon catheter 170 may be inflated. The second balloon catheter 171 is inflated to expand the second expandable tubular member 140 in an amount sufficient to secure the second expandable tubular member 140 within the second lumen 195 and within the branch aperture 135.

As specific applications dictate, the portion of the first tubular stent 110 defining the side branch aperture 135 may be adapted to form a branch securing lip when the branch aperture 135 is expanded a sufficient amount. In one embodiment, the first balloon catheter 170 is inflated before the second balloon catheter 171 is inflated and the first balloon catheter 170 is left inflated until the second expandable tubular member 140 is secured within the branch aperture 135 by the second balloon catheter 171. In another embodiment, the first balloon catheter 170 and the second balloon catheter 171 are inflated simultaneously.

According to an alternative system of the present invention, at least one fixed wire catheter is used to deliver and assemble a bifurcated stent within a bifurcated lumen. FIGS. 10-17 show an embodiment of this alternative system having one fixed wire catheter and one over-the-wire catheter. The fixed wire catheter shown in these figures is an embodiment disclosed in U.S. patent application Ser. No. 10/228,052 filed Aug. 27, 2002, now U.S. Pat. No. 7,172,619, the disclosure of which is incorporated herein by reference. It will be understood that any other suitable fixed wire catheter can be used in place of the fixed wire catheter depicted in the FIGS. 11-16. The use of at least one fixed wire catheter in this system eliminates the use of two guide wires and, in turn, the possibilities of wire crossings which may lead to (1) confusion as to which guide wire terminates in the main vessel and which guide wire terminates in the side branch lumen and/or (2) the two catheters becoming positively stopped at and unable to be advanced beyond the location of the wire crossing. In addition, the use of at least one fixed wire catheter provides a delivery system having a smaller overall profile which enables the system to better navigate constrictions in the vasculature.

Figure 10:
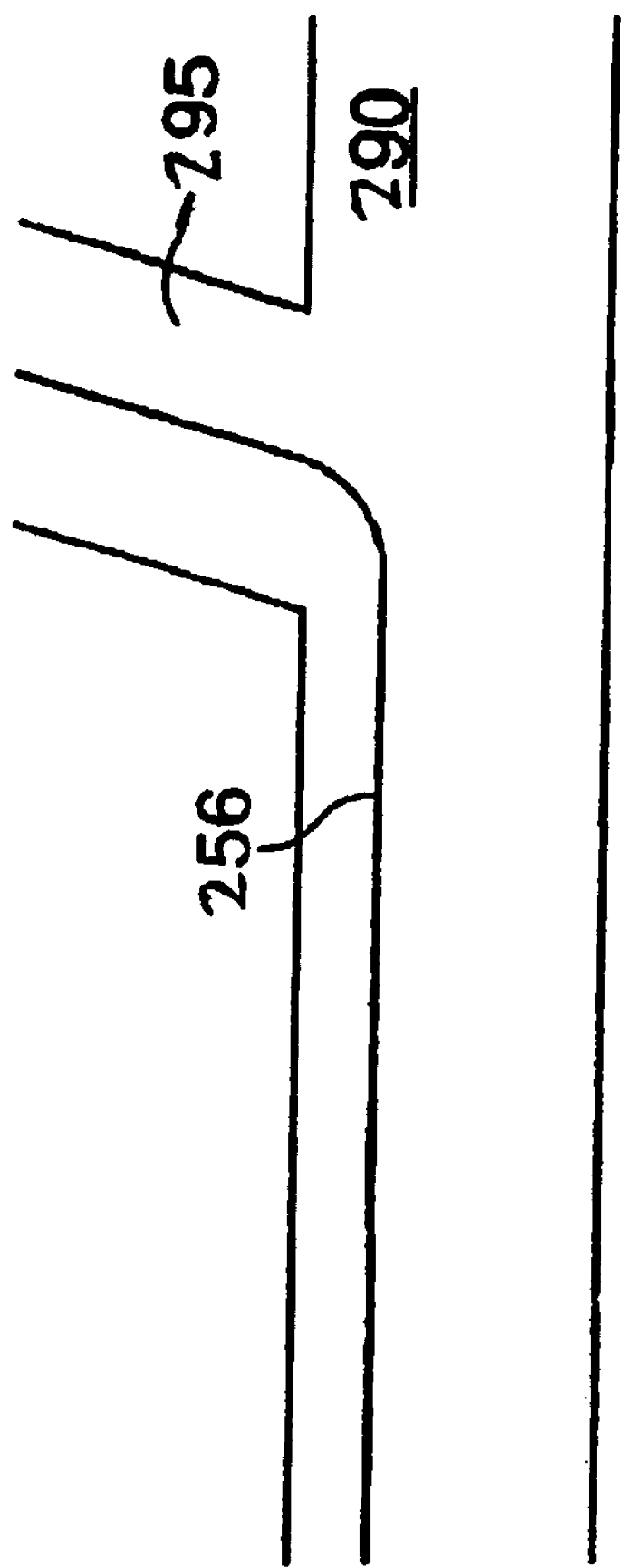
FIG. 10 shows a guide wire disposed in the side branch lumen to be treated.

As shown in FIG. 10, a guide wire 256 is introduced into the side branch lumen at the target site for guiding the over-the-wire catheter 271 into side branch lumen 295. As will be described with reference to FIGS. 11-16, the fixed wire catheter 270 is introduced into main vessel 290 to deliver and assemble the bifurcated stent. As will be described below with regard to FIG. 17, it will be understood that the orientation of the over-the-wire catheter 271 and the fixed wire catheter 270 may be reversed, such that the guide wire 256 is introduced into the main vessel 290 to guide the over-the-wire catheter 271 into the main vessel and the fixed wire catheter 270 is disposed in side branch lumen 295.

Figure 11:
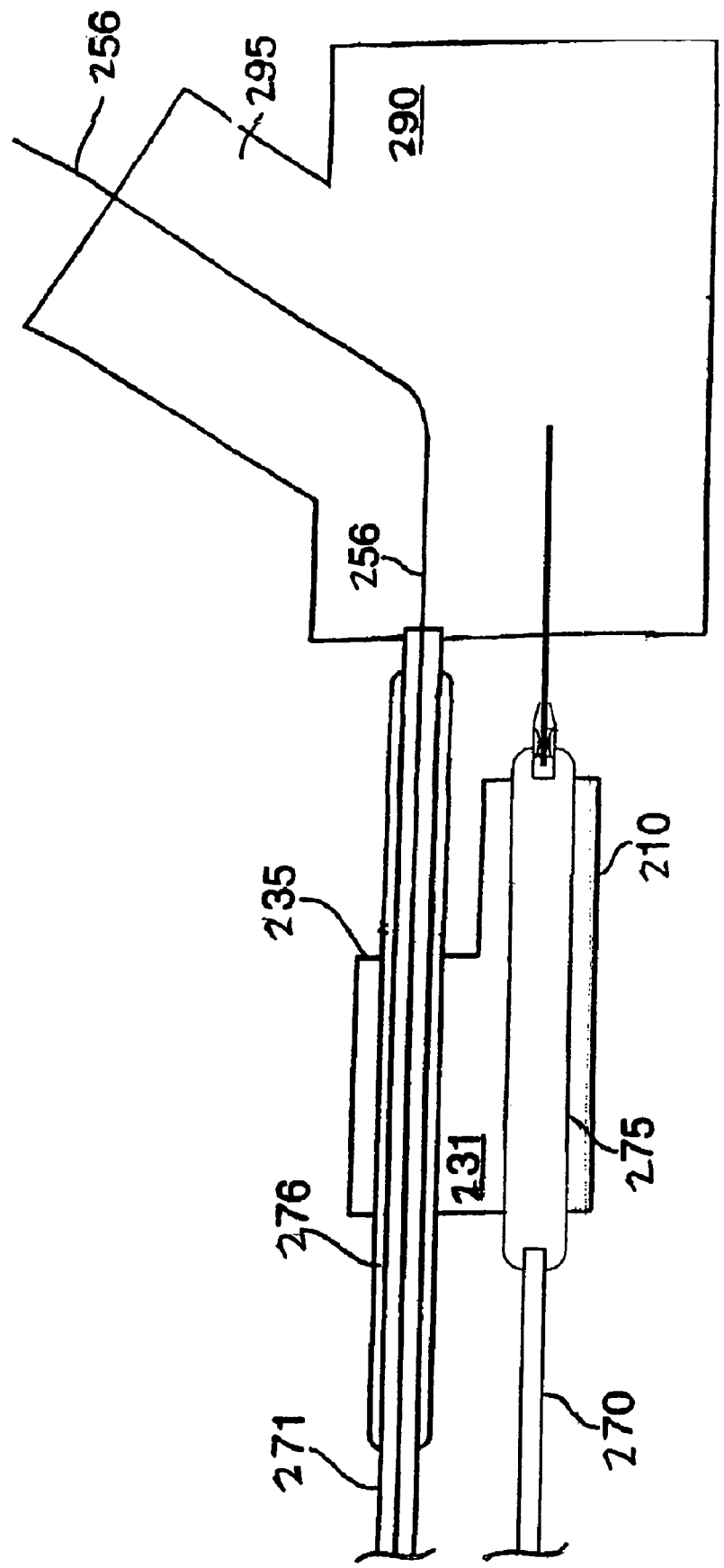
FIG. 11 shows another embodiment of the bifurcated stent delivery system having a fixed wire catheter and an over-the-wire catheter prior to introduction into the lumen to be treated.

As shown in FIG. 11, the balloon 275 of fixed wire catheter 270 is disposed within bore 231 of the balloon expandable stem and first leg portion 210 of a bifurcated stent. Balloon 276 of over-the-wire catheter 271 is also disposed within bore 231 such that a portion of balloon 276 protrudes through aperture 235 and the distal end of balloon 276 extends beyond the distal end of balloon 275. This system is advanced to the treatment site by inserting the proximal end of guide wire 256 into the distal end of the guide wire lumen of catheter 171 and pushing the system along guide wire 256.

Figure 12:
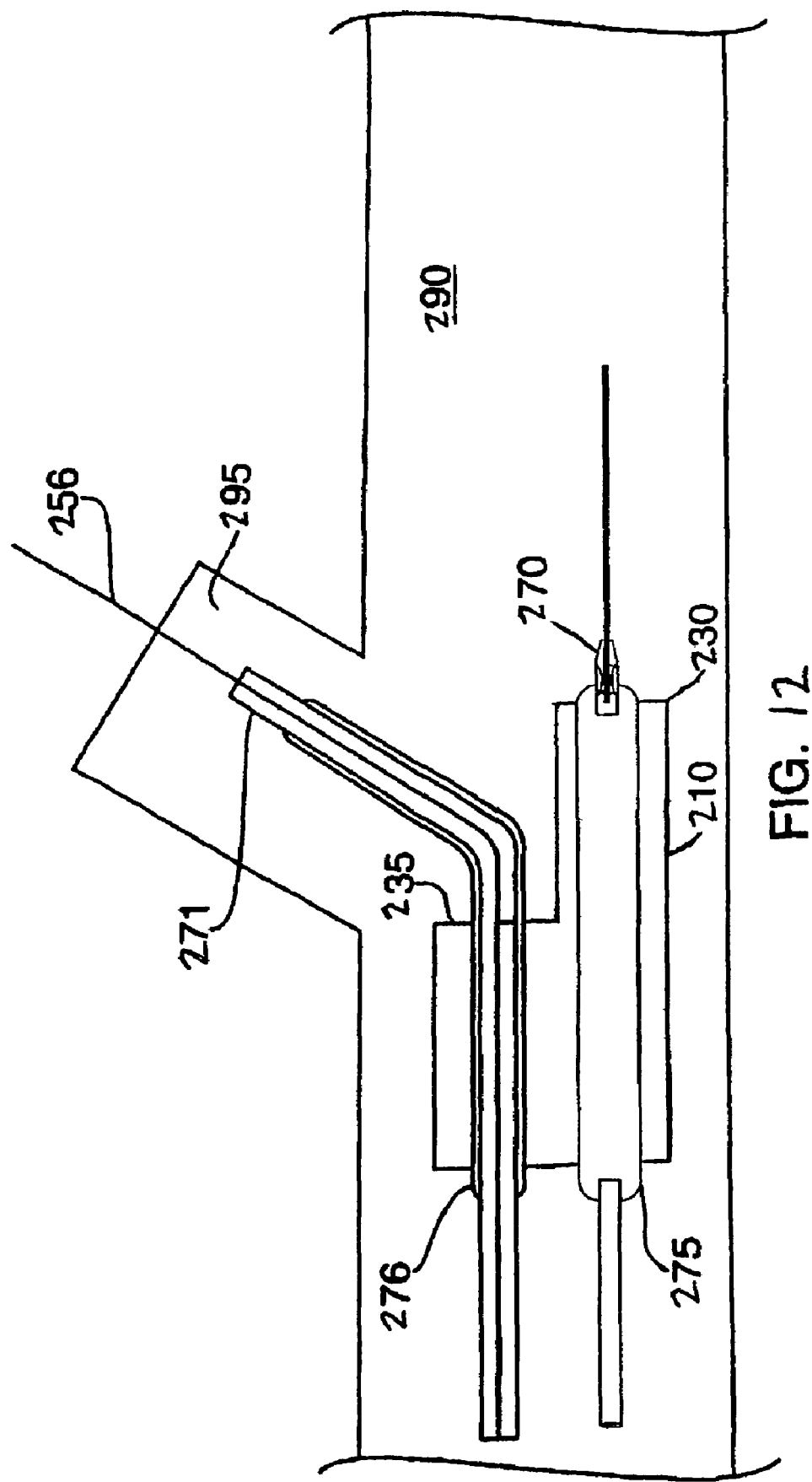
FIG. 12 shows the stem and first leg portion of the bifurcated stent after it has been delivered to the lumen to be treated by the stent delivery system shown in FIG. 11.

As shown in FIG. 12, the system is disposed in the treatment site such that the unexpanded stem and first leg portion 210 are positioned in the main vessel 290 and the branch aperture 235 communicates with the side branch lumen 295. As further shown in FIG. 12, over-the-wire catheter 271 is routed along guide wire 256 such that the distal end of balloon 276 enters side branch lumen 295. This also facilitates the orientation of the system such that branch aperture 235 is aligned with side branch lumen 295.

Figure 13:
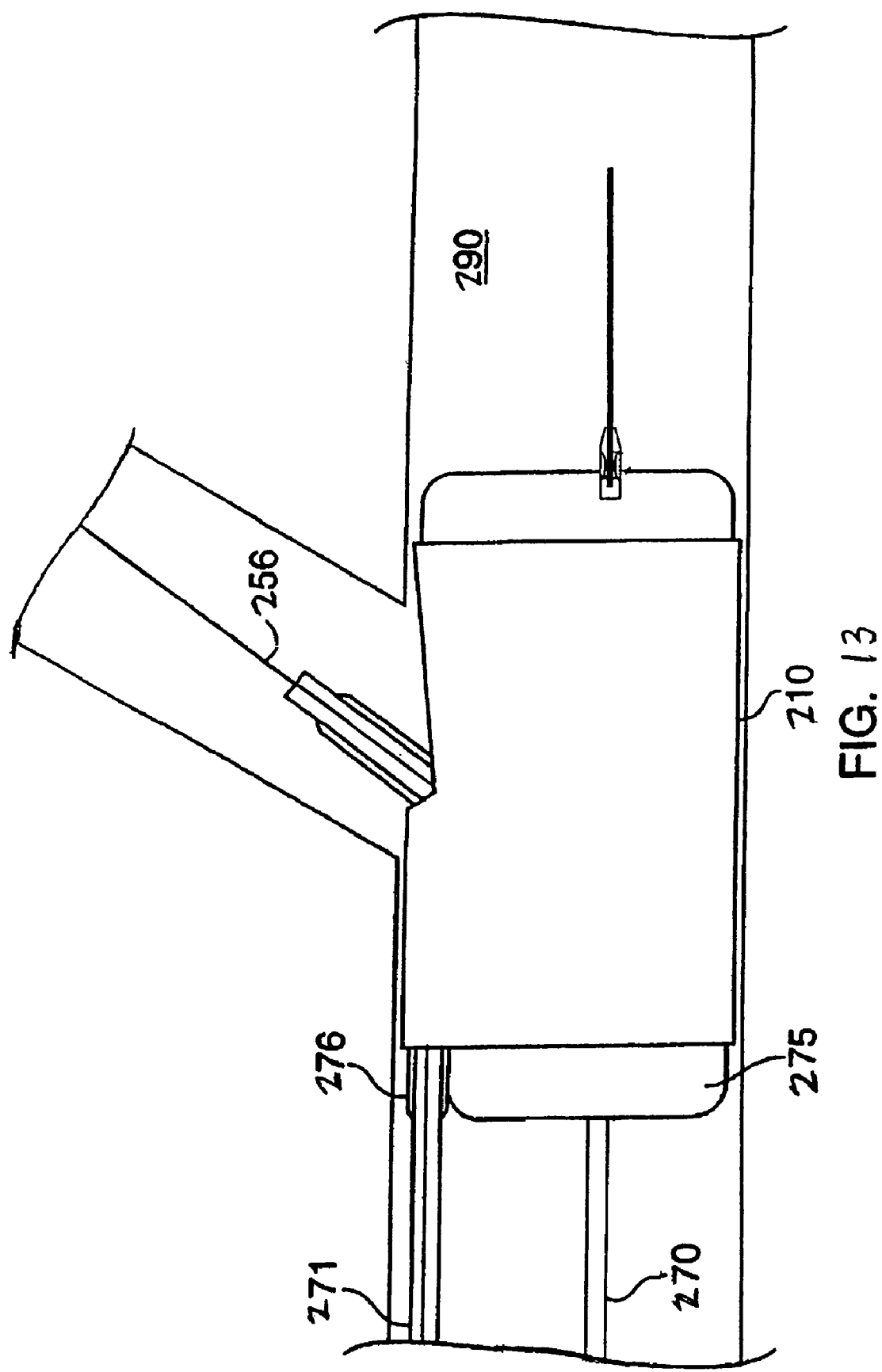
FIG. 13 shows the stem and first leg portion shown in FIG. 12 after it has been expanded.
Figure 14:
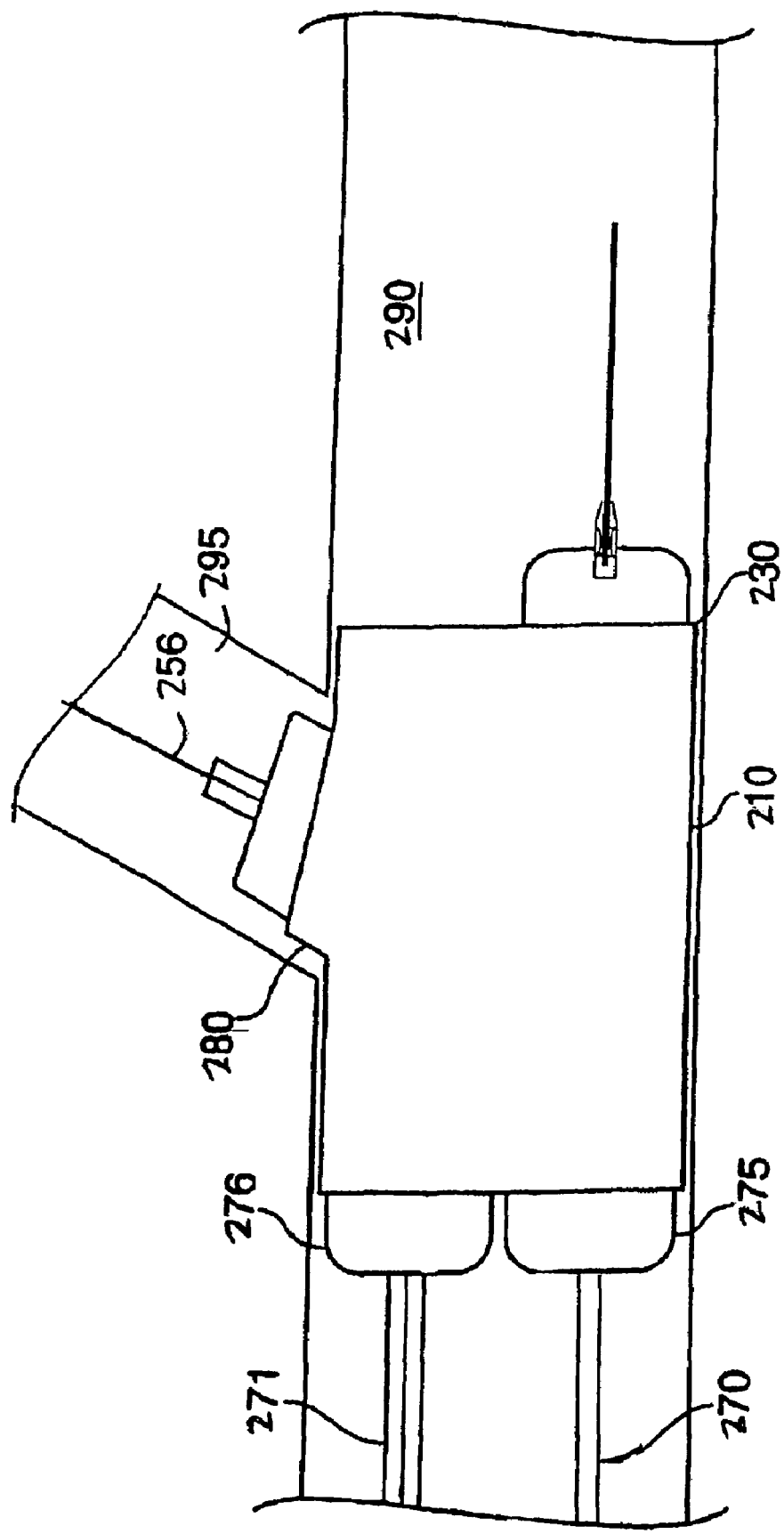
FIG. 14 shows the expansion of the branch aperture.

As shown in FIG. 13, stem and first -leg portion 210 of the bifurcated stent is expanded and implanted into the interior wall of main vessel 290 by inflating balloon 275 of fixed wire catheter 270. As noted above with reference to FIG. 5. a gap between the stem and first leg portion 210 and the interior wall of main vessel 290 has been intentionally included in FIGS. 13-16 for clarity. Referring now to FIG. 14, while balloon 275 is still in an inflated state, balloon 276 of over-the-wire catheter 271 is inflated to enlarge branch aperture 235 such that it matches the dimensions of side branch lumen 295. Further, as the branch aperture 235 is enlarged a portion of the stent defining the branch aperture 235 is pushed outward to form a branch securing lip 280. Balloons 275 and 276 are then deflated and the over-the-wire catheter 271 is withdrawn along guide wire 256 and replaced with another over-the-wire catheter having a second leg portion 240 of the bifurcated stent mounted on the distal end of balloon 276.

Figure 15:
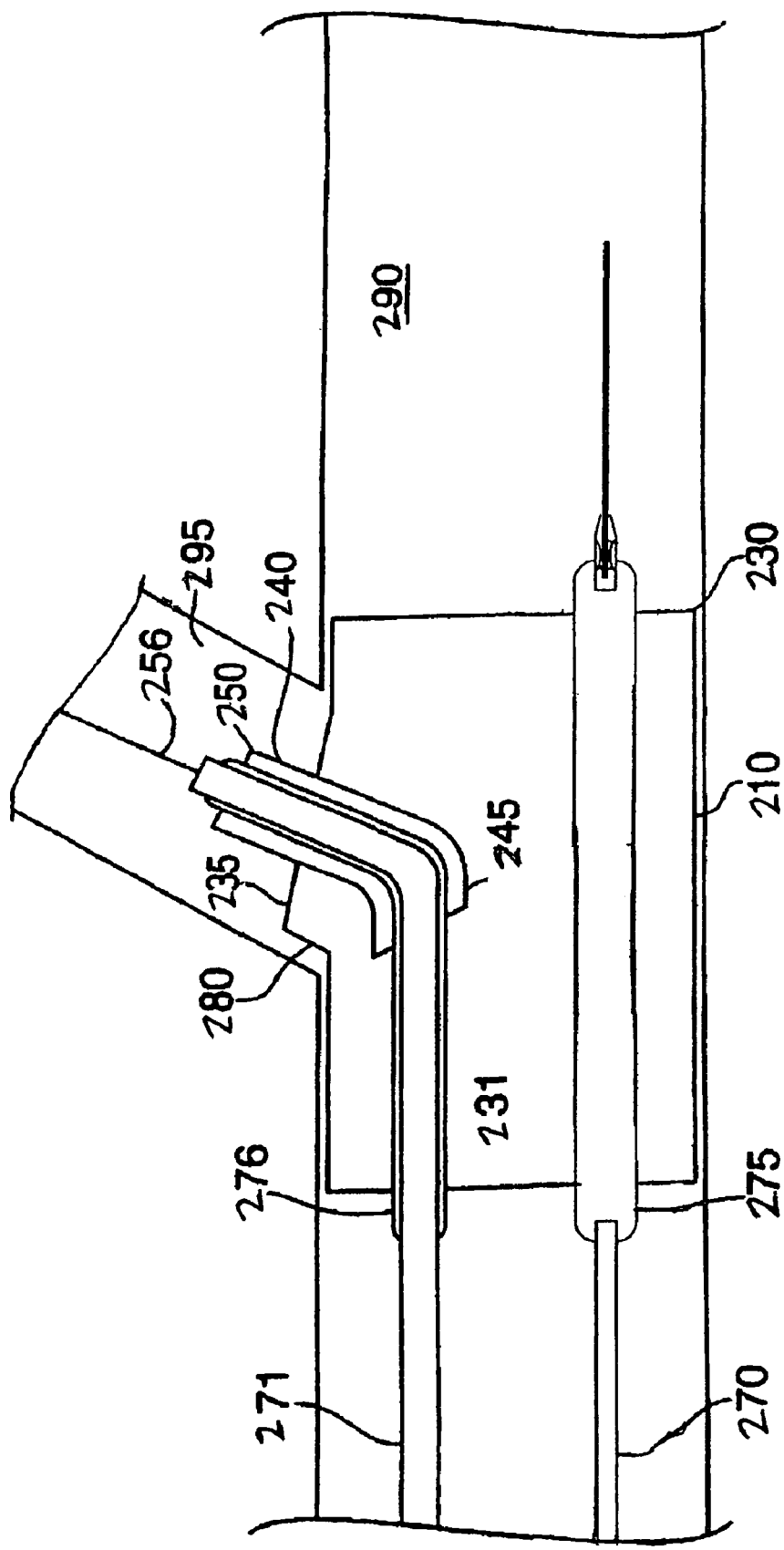
FIG. 15 shows the unexpanded second leg portion of the bifurcated stent after it has been delivered to the branch lumen.

As shown in FIG. 15, over-the-wire catheter 271 is advanced along guide wire 256 into longitudinal bore 231 of the stem and first leg portion 210 and guided through branch aperture 235 so that the distal end 250 of second leg portion 240 protrudes into side branch lumen 295 and the proximal end 245 is positioned within longitudinal bore 131.

Figure 16:
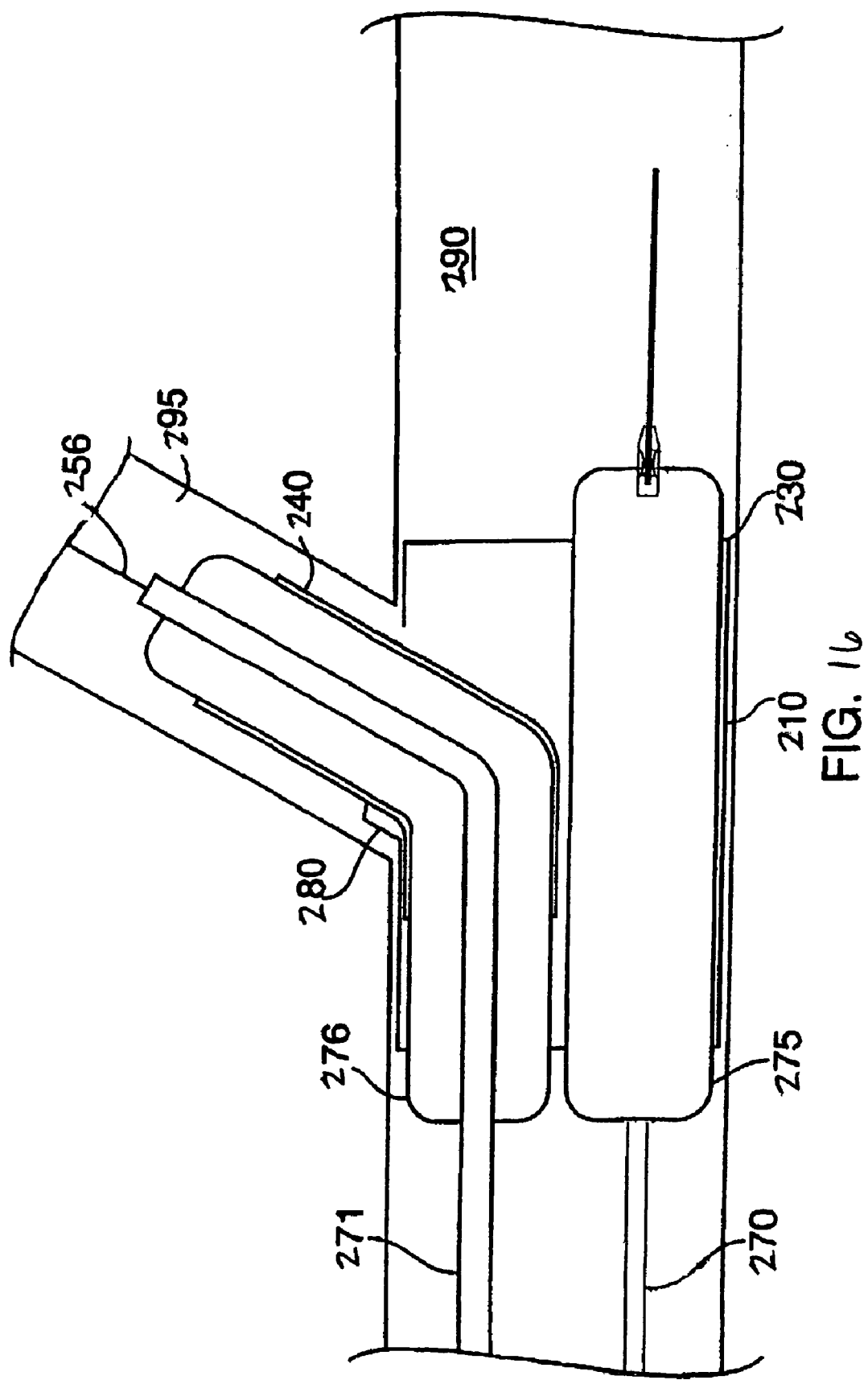
FIG. 16 shows the expansion of the second leg portion of the bifurcated stent in the branch lumen.

As shown in FIG. 16, balloons 275 and 276 of catheters 270 and 271 are partially inflated to substantially equal pressures. The inflation of balloon 276 on catheter 271 causes the second leg portion 240 to expand and implant into the interior wall of side branch lumen 295 completing the assembly of the bifurcated stent. The gap between second leg portion 240 and the interior wall of side branch lumen 295 has been intentionally included in FIG. 16 for clarity. Inflation of balloon 275 of catheter 270 prevents the stem and first leg portion 210 from collapsing when balloon 276 is inflated. The balloons 275 and 276 are then deflated and catheters 270 and 271 are withdrawn.

Figure 17:
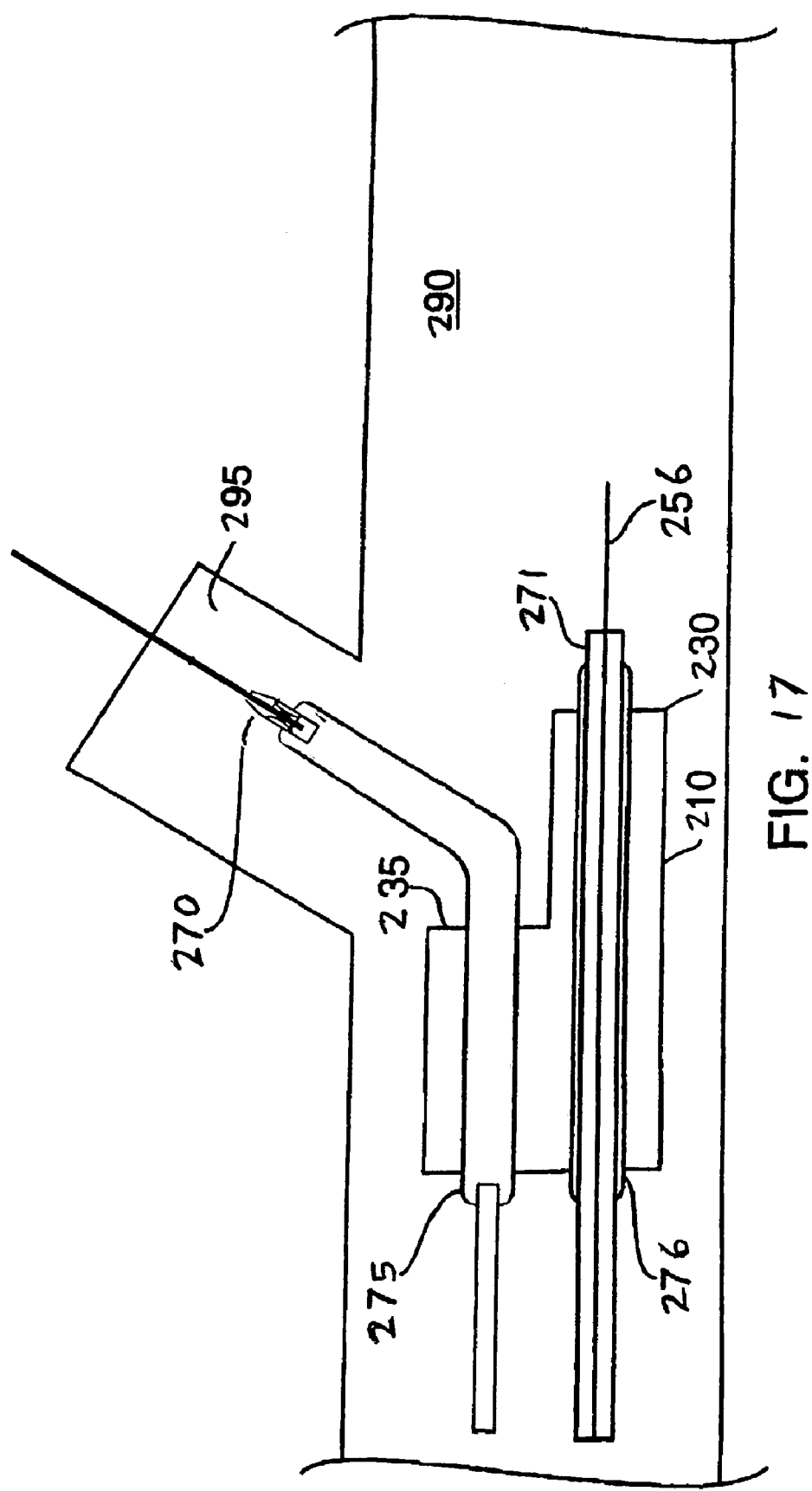
FIG. 17 shows another variation of the embodiment shown in FIGS. 10-16.

FIG. 17 shows a variation of the alternative embodiment described above with reference to FIGS. 10-16. As shown in FIG. 17, the orientation of the orientation of the over-the-wire catheter 271 and the fixed wire catheter 270 has been switched such that the guide wire 256 and over-the-wire catheter 271 extend into the main vessel 290 and the fixed wire catheter 270 extends into the side branch lumen 295.

The procedure for assembling and implanting a bifurcated stent using this arrangement of the over-the-wire catheter 271 and fixed wire catheter 270 follows the same procedure described above with reference to the alternative system shown in FIGS. 10-16. Namely, after the system is disposed at the treatment site with the aperture 235 aligned with the side branch lumen 295, over-the-wire catheter balloon 276 is inflated to expand and implant the stem and first leg portion 210 into the interior wall of main vessel 290. Next, while balloon 276 is still inflated, balloon 275 of fixed wire catheter 270 is inflated to enlarge branch aperture 235 to match the dimensions of side branch lumen 295. Balloons 275 and 276 are then deflated and fixed wire catheter 270 is withdrawn from the vasculature and replaced with another fixed wire catheter having a second leg portion 240 of the bifurcated stent mounted on balloon 275. This fixed wire catheter is advanced through side branch aperture 235 and into the side branch lumen 295 such that the distal end 250 of the second leg portion 240 protrudes into side branch lumen 295 and the proximal end 245 is positioned within the longitudinal bore 231 of the stem and first leg portion 210. Balloons 275 and 276 are partially inflated to substantially equal pressures causing second leg portion 240 to expand and implant into the interior wall of side branch lumen 295. Balloons 275 and 276 are then deflated and catheters 270 and 271 are withdrawn from the vasculature.

It will be understood that a second fixed wire catheter could be used in place of the over-the-wire catheter used for delivering the stem and first leg portion 210 in the alternative systems shown in FIGS. 10-17. In addition, a third fixed wire catheter could be used for delivering the second leg portion 240 in the alternative system shown in FIGS. 10-16.

The stent with which the methods of the present invention may be used can be of any construction that provides first expandable tubular member 110 having a proximal end 115 and a distal end 120 and a longitudinal bore 131 therethrough, with a branch aperture 135 disposed between the proximal end 115 and the distal end 120 communicating with the longitudinal bore 131 of the first expandable tubular member 110 and aperture 135 is sized and adapted to receive and secure a second expandable tubular member 140. Exemplary embodiments of structures which meet this requirement and the method of making them are disclosed in U.S. application Ser.

No. 09/575,957, particularly in FIGS. 22 to 34. The disclosure of Ser. No. 09/575,957 is hereby incorporated by reference in its entirety.

What is claimed is:

1. A method of delivering a stent using a system, said system comprising a fixed wire catheter having a proximal end, a distal end and a first balloon disposed adjacent the distal end; a second catheter having a proximal end, a distal end and a second balloon adjacent the distal end; and a first expandable tubular member mounted on the fixed wire catheter and the second catheter, with said first tubular member having a proximal end forming a stem portion, a distal end forming a first leg portion, a longitudinal bore extending through the stem portion and the first leg portion, and a branch aperture disposed between the proximal end and the distal end, where the distal end of the second catheter extends from the proximal end of the first tubular member through the first leg portion and the distal end of the fixed wire catheter extends from the proximal end of the first tubular member through the branch aperture, the method comprising:
   a) delivering the first expandable tubular member, fixed wire balloon catheter and second balloon catheter to a bifurcated vessel having a first lumen and a second lumen;
   b) advancing the distal end of the fixed wire catheter into the second lumen; and
   c) inflating the first balloon sufficiently to align the branch aperture with the second lumen and to form a branch securing lip at the branch aperture of the first expandable tubular member.

2. The method according to claim 1, where the second catheter is an over-the-wire catheter.

3. The method according to claim 1, where the second catheter is a fixed wire catheter.

4. The method according to claim 1, further comprising delivering a second expandable tubular member having a proximal end, a distal end and a longitudinal bore extending therethrough into the branch aperture so that the distal end of the second expandable tubular member is disposed within the second lumen and the proximal end of the second expandable tubular member is disposed within the branch aperture of the first tubular member and the longitudinal bore of the second expandable tubular member in fluid communication with the longitudinal bore of the first expandable tubular member.

5. A method of delivering a stent to a bifurcated vessel having a first lumen and a second lumen using a system, said system comprising a fixed wire catheter having a proximal end, a distal end and a first balloon disposed adjacent the distal end and an over-the-wire catheter having a proximal end, a distal end and a second balloon disposed adjacent the distal end, whereby the over-the-wire catheter comprises a guide wire and a first expandable tubular member is mounted on the fixed wire catheter and the over-the-wire catheter, with said first expandable tubular member having a proximal end forming a stem portion, a distal end forming a first leg portion, and a branch aperture disposed between the proximal end and the distal end, the branch aperture communicating with the longitudinal bore, wherein the over-the-wire catheters extends through the longitudinal bore defined by the stem portion and first leg portion of the first expandable tubular member and the fixed-wire catheter extends through the longitudinal bore defined by the stem portion of the first expandable tubular member and through the branch aperture, with the method comprising:
   a) delivering a guide wire into the first lumen;
   b) delivering the first expandable tubular member to the first lumen of the bifurcated vessel;
   c) inflating the balloon of the over-the-wire catheter in an amount sufficient to secure the first expandable member in the first lumen;
   d) inflating the balloon of the fixed wire catheter in an amount sufficient to align the branch aperture with the second lumen;
   e) removing the over-the-wire catheter;
   f) delivering a second expandable tubular member mounted on a third catheter, said second expandable tubular member having a proximal end, a distal end and a longitudinal bore extending therethrough, into the branch aperture so that the distal end of the second expandable tubular member is disposed within the second lumen and the proximal end of the second expandable tubular member is disposed within the branch aperture of the first tubular member, the longitudinal bore of the second expandable tubular member in fluid communication with the longitudinal bore of the first expandable tubular member; and
   g) inflating the balloon of the third catheter to expand the second expandable tubular member in an amount sufficient to secure the second expandable tubular member within the lumen and within the branch aperture.

6. A system for delivering a stent comprising:
   a) a first expandable tubular member having a proximal end forming a stem portion, a distal end forming a first leg portion and a longitudinal bore extending therethrough, the first tubular member having a branch aperture disposed between the proximal end and the distal end and adapted to form a branch securing lip upon expansion of a balloon catheter extending through the longitudinal bore defined by the stem portion and through the branch aperture;
   b) a fixed wire catheter having proximal end, a distal end and a first balloon disposed adjacent the distal end; and
   c) a second catheter having a proximal end, a distal end and a second balloon disposed adjacent the distal end, wherein one of the fixed wire catheter or second catheter extends through the longitudinal bore defined by the stem portion of the first expandable tubular member and through the branch aperture and the other of said catheters extends through the longitudinal bore defined by the stem portion and first leg portion of the first expandable tubular member.

7. The system according to claim 6, further comprising:
   d) a second expandable tubular member mounted on a third catheter having a proximal end, a distal end and a third balloon disposed adjacent the distal end of said third catheter, said second expandable tubular member having a proximal end, a distal end and a longitudinal bore therethrough and having a diameter permitting the proximal end of the second expandable tubular member to be securely disposed within the branch aperture of the first tubular member upon expansion, with the longitudinal bore of the second expandable tubular member in fluid communication with the longitudinal bore of the first longitudinal member.

8. The system according to claim 6, wherein the second catheter comprises a fixed wire catheter.

9. The system according to claim 7, wherein the third catheter comprises a fixed wire catheter.

10. A method of delivering a stent using a system, said system comprising a fixed wire catheter having a proximal end, a distal end and a first balloon disposed adjacent the distal end; a second catheter having a proximal end, a distal end and a second balloon adjacent the distal end; and a first expandable tubular member mounted on the fixed wire catheter and the second catheter, with said first tubular member having proximal end forming a stem portion, a distal end forming a first leg portion, a longitudinal bore extending through the stem portion and the first leg portion, and a branch aperture disposed between the proximal end and the distal end, where the distal end of the fixed wire catheter extends from the proximal end of the first tubular member through the first leg portion and the distal end of the second catheter extends from the proximal end of the first tubular member through the branch aperture, the method comprising:

a) delivering the first expandable tubular member, fixed wire balloon catheter and second balloon catheter to a bifurcated vessel having a first lumen and a second lumen;

b) advancing the distal end of the second catheter into the second lumen; and c) inflating the balloon of the second catheter sufficiently to align the branch aperture with the second lumen and to form a branch securing lip at the branch aperture of the first expandable tubular member.

11. The method according to claim 10, further comprising delivering a second expandable tubular member having a proximal end, a distal end and a longitudinal bore extending therethrough into the branch aperture so that the distal end of the second expandable tubular member is disposed within the second lumen and the proximal end of the second expandable tubular member is disposed within the branch aperture of the first tubular member and the longitudinal bore of the second expandable tubular member in fluid communication with the longitudinal bore of the first expandable tubular member.

12. The method according to claim 10, wherein the second catheter comprises an over-the-wire catheter.

* * * * *

UNITED STATES PATENT AND TRADEMARK OFFICE
CERTIFICATE OF CORRECTION

| | |
|---|---|
| PATENT NO. | : 7,641,685 B2 |
| APPLICATION NO. | : 11/478716 |
| DATED | : January 5, 2010 |
| INVENTOR(S) | : Jacob Richter |

It is certified that error appears in the above-identified patent and that said Letters Patent is hereby corrected as shown below:

Page 2 under "Foreign Patent Documents" foreign reference SU 942736 should read "RU" 942736

Column 2, line 47, please remove "one" from the sentence "...balloon is to be disposed in the main vessel, and one the..."

Column 2, line 60, please amend "solves" to read "solve"

Column 3, line 50, please amend the "." after "FIG. 11." to read a ";" such as "FIG. 11;"

Column 7, line 48, please remove the "-" from "first-leg" to read "first leg"

Signed and Sealed this

First Day of June, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,641,685 B2 | Page 1 of 1 |
| APPLICATION NO. | : 11/478716 | |
| DATED | : January 5, 2010 | |
| INVENTOR(S) | : Jacob Richter | |

It is certified that error appears in the above-identified patent and that said Letters Patent is hereby corrected as shown below:

Title page, item (*) Notice: Subject to any disclaimer, the term of this patent is extended or adjusted under 35 U.S.C. 154(b) by 434 days.

Delete the phrase "by 434 days" and insert -- by 481 days --.

Signed and Sealed this

Seventeenth Day of August, 2010

David J. Kappos
*Director of the United States Patent and Trademark Office*